United States Patent
Bruneau et al.

(10) Patent No.: US 7,468,064 B2
(45) Date of Patent: Dec. 23, 2008

(54) SYSTEMS AND METHODS FOR POSITIONING IMPLANTS RELATIVE TO BONE ANCHORS IN SURGICAL APPROACHES TO THE SPINE

(75) Inventors: Aurelian Bruneau, Memphis, TN (US); Anthony J. Melkent, Germantown, TN (US); John D. Pond, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 855 days.

(21) Appl. No.: 10/645,457

(22) Filed: Aug. 21, 2003

(65) Prior Publication Data

US 2005/0043742 A1 Feb. 24, 2005

(51) Int. Cl.
*A61B 17/58* (2006.01)
*A61B 17/60* (2006.01)

(52) U.S. Cl. ...................................................... 606/99
(58) Field of Classification Search .................... 606/99, 606/104, 96, 98, 80, 70, 71, 72, 73
See application file for complete search history.

(56) References Cited

U.S. PATENT DOCUMENTS

| | | | |
|---|---|---|---|
| 2,242,003 A | 5/1941 | Lorenzo | |
| 2,414,882 A | 1/1947 | Longfellow | |
| 4,383,527 A | 5/1983 | Asnis et al. | |
| 4,537,185 A | 8/1985 | Stednitz | |
| 4,653,489 A | 3/1987 | Tronzo | |
| 4,790,297 A | 12/1988 | Luque | |
| 4,913,134 A | 4/1990 | Luque | |
| 5,015,247 A * | 5/1991 | Michelson | 606/61 |
| 5,047,030 A | 9/1991 | Draenert | |
| 5,171,279 A | 12/1992 | Mathews et al. | |
| 5,192,282 A | 3/1993 | Draenert | |
| 5,584,887 A | 12/1996 | Kambin | |
| 5,653,710 A | 8/1997 | Harle | |
| 5,665,092 A | 9/1997 | Leibinger et al. | |
| 5,810,817 A | 9/1998 | Roussouly et al. | |
| 5,871,484 A | 2/1999 | Spievack et al. | |
| 6,175,760 B1 | 1/2001 | Baskin et al. | |
| 6,210,376 B1 | 4/2001 | Grayson | |
| 6,214,012 B1 | 4/2001 | Karpman et al. | |
| 6,235,028 B1 * | 5/2001 | Brumfield et al. | 606/53 |
| 6,287,313 B1 | 9/2001 | Sasso | |
| 6,440,133 B1 * | 8/2002 | Beale et al. | 606/61 |
| 6,517,565 B1 * | 2/2003 | Whitman et al. | 606/219 |
| 6,530,926 B1 | 3/2003 | Davison | |
| 6,589,244 B1 * | 7/2003 | Sevrain et al. | 606/72 |
| 6,610,065 B1 * | 8/2003 | Branch et al. | 606/84 |
| 6,746,454 B2 * | 6/2004 | Winterbottom et al. | 606/99 |
| 2001/0021852 A1 | 9/2001 | Chappius | |
| 2004/0147928 A1 * | 7/2004 | Landry et al. | 606/61 |

FOREIGN PATENT DOCUMENTS

WO WO 01 10324 A 2/2001
WO WO 01/41681 A1 6/2001

* cited by examiner

*Primary Examiner*—Pedro Philogene
(74) *Attorney, Agent, or Firm*—Krieg DeVault

(57) ABSTRACT

Devices, instruments, systems and techniques for guiding an implant to a location adjacent a bone anchor include a guide member with a connecting portion and a guiding portion. The connecting portion is adjacent the bone anchor, and the guiding portion extends proximally from the connecting portion and is adapted guide an implant therealong toward the bone anchor. The guiding portion is flexible to facilitate manipulation and implant placement in the patient's body.

29 Claims, 6 Drawing Sheets

SYSTEMS AND METHODS FOR POSITIONING IMPLANTS RELATIVE TO BONE ANCHORS IN SURGICAL APPROACHES TO THE SPINE

BACKGROUND

Techniques and systems have been developed for stabilizing and correcting deformities in the spinal column and for facilitating fusion at various levels of the spine. Some techniques include positioning a longitudinal element along the spinal column and engaging the longitudinal element to the spine with bone fasteners. Other techniques require the assembly of components of either the fasteners or the stabilization construct adjacent the spinal column.

It is desirable to minimize the intrusion into the muscle, tissue, nerves and other anatomical structures during spinal surgery. Minimally invasive techniques reduce trauma, facilitate healing, and reduce post-operative recovery time for the patient.

Accordingly, there remains a need for systems and methods to facilitate minimally invasive surgical techniques for positioning implants adjacent the spinal column. Such systems and techniques may also have application in open surgical techniques. The present invention is directed to meeting these needs, among others.

DESCRIPTION OF THE ILLUSTRATED EMBODIMENTS

Figure 1:
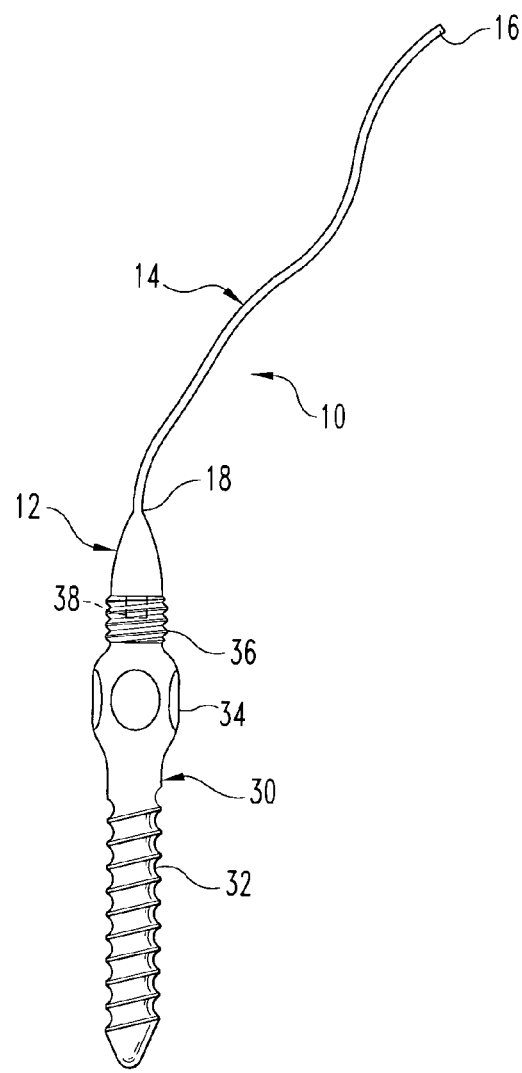
FIG. 1 is an elevation view of one embodiment bone anchor including a guide member secured thereto.

For the purposes of promoting an understanding of the principles of the invention, reference will now be made to embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 1, there is shown a guide member 10 including a connecting portion 12 and a guiding portion 14. Connecting portion 12 is positionable adjacent to a bone anchor, such as bone anchor 30. Guiding portion 14 extends proximally from connecting portion 12 and is adapted to guide an implant therealong to a position more adjacent anchor 30. Guiding portion 14 is flexible to facilitate placement of the implant adjacent to anchor 30 in minimally invasive surgical approaches and other approaches where use of flexible guiding portion 14 may be desirable. The flexible guiding portion 14 can be readily manipulated to bend around tissue, other anatomical structures located between the anchor and the opening in the skin of the patient, instruments, and/or access portals through which the implant is to be positioned. The implant can then be moved along guiding portion 14 with guiding portion 14 directing the implant into alignment with anchor 30.

In the illustrated embodiment, anchor 30 is a bone screw having a distally threaded shaft 32 and an intermediate tool engaging portion 34. Head portion 36 extends proximally from intermediate portion 34. Head portion 36 is engageable with or integrally formed with connecting portion 12. In the illustrated embodiment, head portion 36 includes an internally threaded receptacle 38 for engagement with connecting portion 12. Head portion 36 further includes an externally threaded portion to facilitate attachment of an implant thereto, as discussed further below. Other forms for anchor 30 are also contemplated. Anchor 30 can be in the form of a hook, bolt, interference anchor, or staple, for example. In still another embodiment, anchor 30 can be provided with a head portion 36 that is smooth, pitted, threaded, serrated, grooved, or combinations thereof.

In the illustrated embodiment, connecting portion 12 is releasably engageable to anchor 30. Other embodiments contemplate connecting portion 12 that is permanently affixed or engaged to the anchor. In such embodiments, connecting portion 12 can remain, alone or in combination with guiding portion 14, in the patient after surgery. It is further contemplated that connecting portion 12 and/or guiding portion 14 can be made from resorbable material, or non-resorbable material. In still another embodiment, after guiding the implant into position relative to the anchor, guide member 10 is severed along at least one of guiding portion 14 or connecting portion 12.

Figure 2:
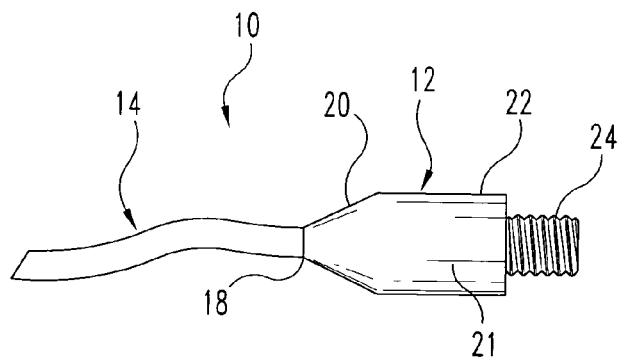
FIG. 2 is an elevation view of a distal portion of the guide member of FIG. 1.

As further shown in FIG. 2, guiding member 10 includes connecting portion 12 having a body 22 with a proximal tapered portion 20 and a cylindrical distal portion 21. Guiding portion 14 is coupled with and extends proximally from body 22 at its proximal end 18. Tapered portion 20 provides a smooth transition between the relatively small diameter guiding portion 14 and the head of anchor 30, facilitating implant placement thereover and guiding its placement to anchor 30. In one embodiment, it is contemplated that guiding portion 14 includes a cross-sectional dimension that is less than half of the maximum cross-sectional dimension of connecting portion 12. Other embodiments contemplate that guiding portion 14 includes a cross-sectional dimension that is less than one-fourth of the maximum cross-sectional dimension of connecting portion 12. Still other embodiment contemplate a guiding portion 14 that includes a cross-sectional dimension that greater than one-half of the maximum cross-sectional dimension of connecting portion 12.

A connector 24 extends distally from body 22. Connector 24 is engageable to a proximal portion of anchor 30. It is contemplated that connecting portion 12 provides a rigid connection with anchor 30, and guiding portion 14 is movable universally relative to connecting portion 12 to define an insertion pathway to anchor 30. Connector 24 can be threaded for threaded engagement with receptacle 38 of anchor 30, as shown in FIGS. 1 and 2.

Figure 3:
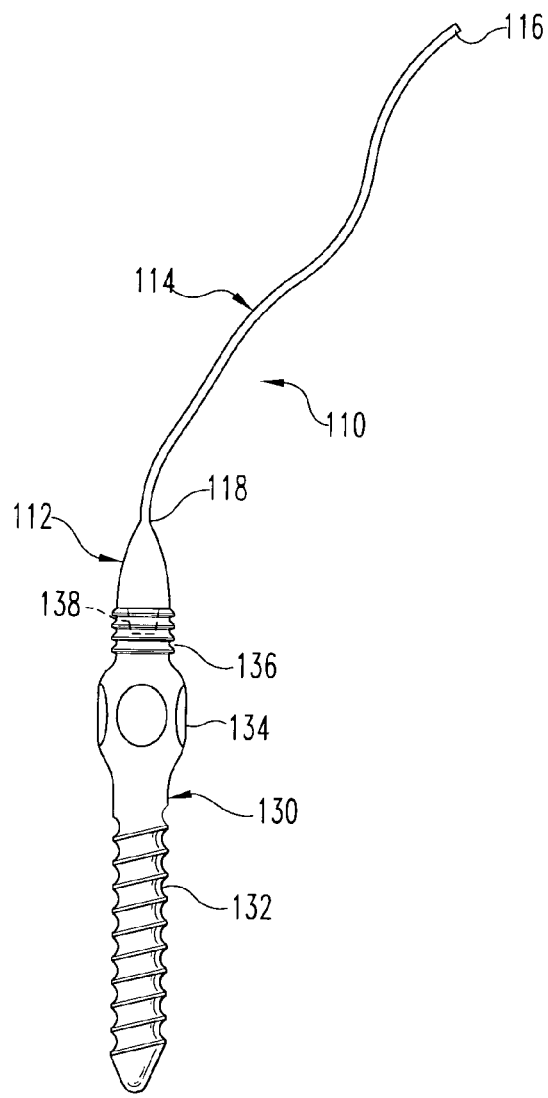
FIG. 3 is an elevation of another embodiment bone anchor with another embodiment guide member secured thereto.
Figure 4:
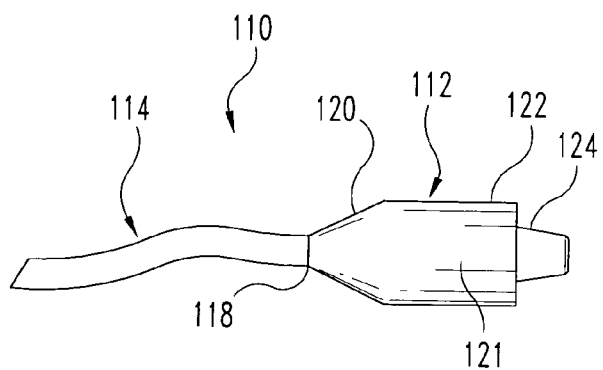
FIG. 4 is an elevation view of a distal portion of the guide member of FIG. 3.

In the FIGS. 3 and 4, another embodiment guide member 110 includes a connecting portion 112 releasably engageable to anchor 130. Anchor 130 includes a distally threaded shaft 132 and an intermediate tool engaging portion 134. Head portion 136 extends proximally from intermediate portion 134. Head portion 136 is engageable with or integrally formed with connecting portion 112. In the illustrated embodiment, head portion 136 includes an internally tapered receptacle 138 for engagement with connecting portion 112. Head portion 136 further includes an externally threaded portion to facilitate attachment of an implant thereto, as discussed further below.

Guiding portion 114 extends proximally from connecting portion 112 and is coupled to body 122 at proximal end 118. Guiding portion 114 is flexible to facilitate its use in minimally invasive procedures and other procedures where flexible guiding portion 114 may be desirable. Connecting portion 112 includes a body 122 having a proximal tapered portion 120 and a cylindrical distal portion 121. Tapered portion 120 provides a smooth transition between the relatively small diameter guiding portion 114 and the head of anchor 130, facilitating implant placement thereover. A connector 124 extends distally from body 122. Connector 124 is tapered distally and frictionally engageable in the internally tapered receptacle 138 of anchor 130 for a press fit therewith.

For embodiments in which guide member 10, 110 is releasably engaged with the anchor, body 22, 122 can be adapted for engagement by a tool to apply an engaging and/or disengaging force thereto. For example, body 22 can include a hex configuration to assist in the application of a rotational force to threadingly engage connector 24 to anchor 30. In another example, body 122 can receive an impaction or pressing force on proximal portion 120 to seat connector 124 in frictional engagement with receptacle 138 of anchor 130. Body 122 can be slotted or include other configurations that allow a proximal removal force to be applied thereto. Guide member 110 could also be removed by pulling proximally on flexible guiding portion 114.

The flexible guiding portions 14, 114 can be integral with, releasably coupled, or permanently coupled with the respective connecting portion 12, 112. Guiding portions 14, 114 can in the form of a cable, wire, thread, suture, strand, tether or other suitable flexible member, for example. Connecting portions 12, 112 can be made from the same or different material than guiding portions 14, 114.

Figure 5:
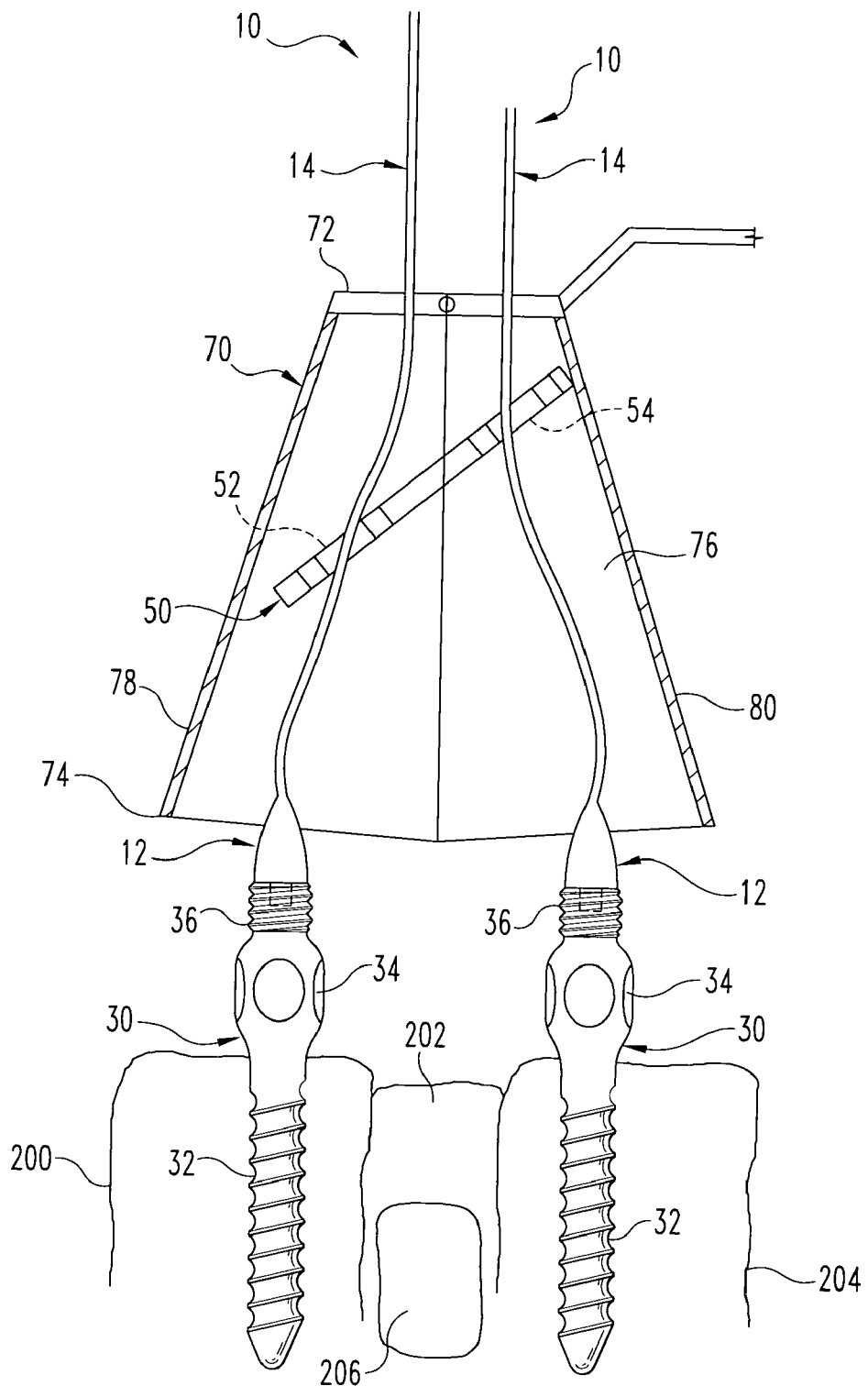
FIG. 5 is an elevation view showing a portion of one technique using the guide member for positioning an implant adjacent the spinal column in a minimally invasive approach.

The guide members described herein have application in minimally invasive surgical procedures. One example of an application is provided with reference to FIGS. 5-7, anchor 30, and guide member 10. Vertebrae 200, 204 are accessed in a minimally invasive approach with retractor 70. Retractor 70 can be inserted over a dilator comprising one of a number of sequentially inserted dilators that dilate an incision to provide an access portal to vertebrae 200, 204. Any approach to the spinal column is contemplated, including anterior, posterior, lateral, antero-lateral, anterior-oblique, and postero-lateral approaches, for example. The spinal column can be approached in any of its regions, including the cervical, thoracic, lumbar and sacral regions.

In the illustrated embodiment, retractor 70 includes a working channel or passage 76 extending between a proximal end 72 and a distal end 74. Working channel 74 includes a reduced size configuration (not shown) for insertion formed by first portion 78 and second portion 80 of retractor 70. First and second portions 78, 80 can be separated or pivoted away from one another so that distal end 74 is enlarged to provide a frusto-conical shape to working channel 76 and facilitate greater access to the surgical site adjacent distal end 74. Other minimally invasive access instruments and techniques are also contemplated, including non-expandable tissue retractors, cannulas, micro-incisions and punctures. The present invention also has application in non-minimally invasive approaches to the spine.

First and second bone anchors 30 are engaged to respective ones of the vertebrae 200, 204 either prior to or after insertion of retractor 70. A disc space 202 between vertebrae 200, 204 can include an interbody implant 206 inserted through retractor 70 or inserted prior to placement of retractor 70. Interbody implant 206 can be an artificial disc device, graft material, fusion device, or other interbody spacer device. It is further contemplated that disc space 202 does not include any implant located therein.

Anchors 30 can be inserted through retractor 70 and engaged to vertebra 200, 204. Alternatively, anchors 30 can be guided through respective skin incisions and engaged to respective ones of the vertebrae 200, 204. For example, anchors 30 can be cannulated and guided to the desired location on vertebrae 200, 204 with a guide wire under fluoroscopy, or other suitable viewing and/or guiding means. Retractor 70, if employed, can then be positioned and enlarged over the implanted anchors 30. Guide members 10 can then be secured to respective ones of the anchors 30.

An implant 50 can then be guided with guide members 10 through retractor 70 for engagement with anchors 30. In the illustrated embodiment, implant 50 is a plate having first passage 52 and second passage 54. Other types of implants are also contemplated that can be guided into position with guide member 10, including extravertebral implants such as plates, rods, set screws, staples, engagement members, and components of bone anchors. It is further contemplated that intervertebral implants and devices positioned in the space between vertebrae can be guided into position with guide member 10. The guided implants can be rigid, flexible or combinations thereof. The guide members can also be employed along multiple levels of the spine. For example, implant 50 can be a plate having a length adapted to extend along at least three vertebrae.

Guiding portions 14 of guide members 10 of each anchor 30 can extend through the proximal end 72 of retractor 70 for positioning through respective ones of the passages 52, 54. Implant 50 can then be manipulated through the proximal end opening of retractor 70 and positioned into working channel 76. Implant 50 is moved along guiding portions 14 to guide implant 50 through the proximal end opening of retractor 70 to anchors 30.

Figure 6:
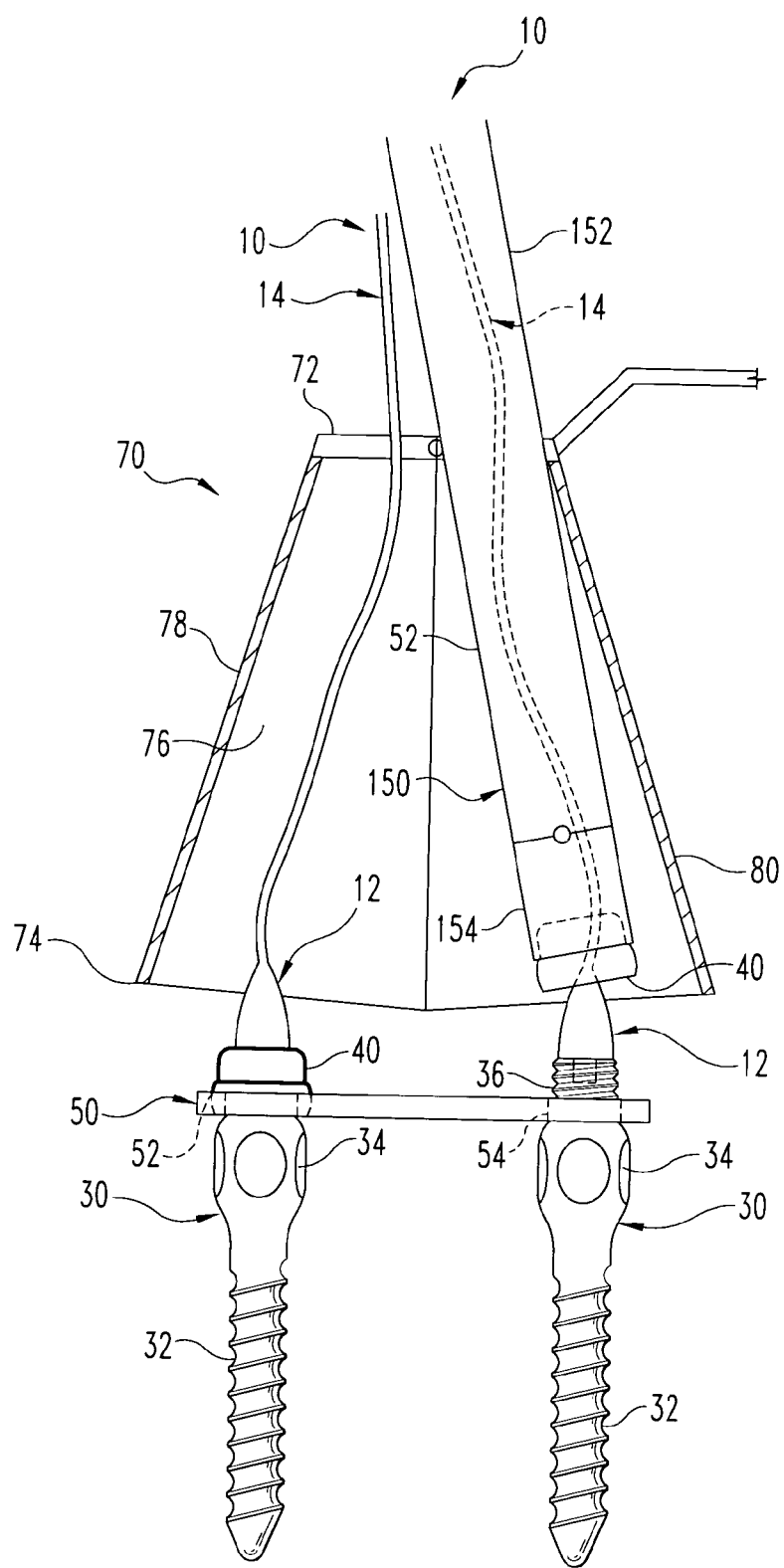
FIG. 6 is an elevation view showing another portion of the technique using the guide member for positioning an implant adjacent the spinal column in a minimally invasive approach.

Implant 50 is moved distally along guiding portions 14 of guide members 10 until proximal head portions 36 of anchors 30 are positioned through respective ones of the passage 52, 54. The tapered proximal portion 20 of body 22 of each guide member 10 can facilitate centering of passage 52, 54 over the proximal portions 36 of anchors 30. An engagement member 40, secured to the distal end of driving instrument 150 in FIG. 6, is engaged to proximal head portions 36 to secure implant 50 to anchors 30.

In the illustrated embodiment, driving instrument 150 includes a proximal shaft 152 and an articulated distal end portion 154. The articulated distal end portion 154 allows shaft 152 to be angled relative to the central axis of anchor 30 for engagement of engagement member 40 from an approach along guiding portion 14. Driving instrument 150 is positionable in working channel 76 of retractor 70 with engagement member 40 releasably secured at its distal end. Driving instrument 150 includes a central passage through shaft 152 and distal end 154 for receiving guiding portion 14 at least partially therethrough. Engagement member 40 also includes a passage for receiving guiding portion 14. Engagement member 40 is engaged to the proximal end of anchor 30 to secure implant 50 thereto.

Engagement member 40 can be an internally threaded nut as shown in the illustrated embodiment. Other embodiments contemplate other forms for engagement member 40, including clamping mechanisms, wedge mechanisms, collars, or other device suitable to secure an implant to an anchor.

Figure 7:
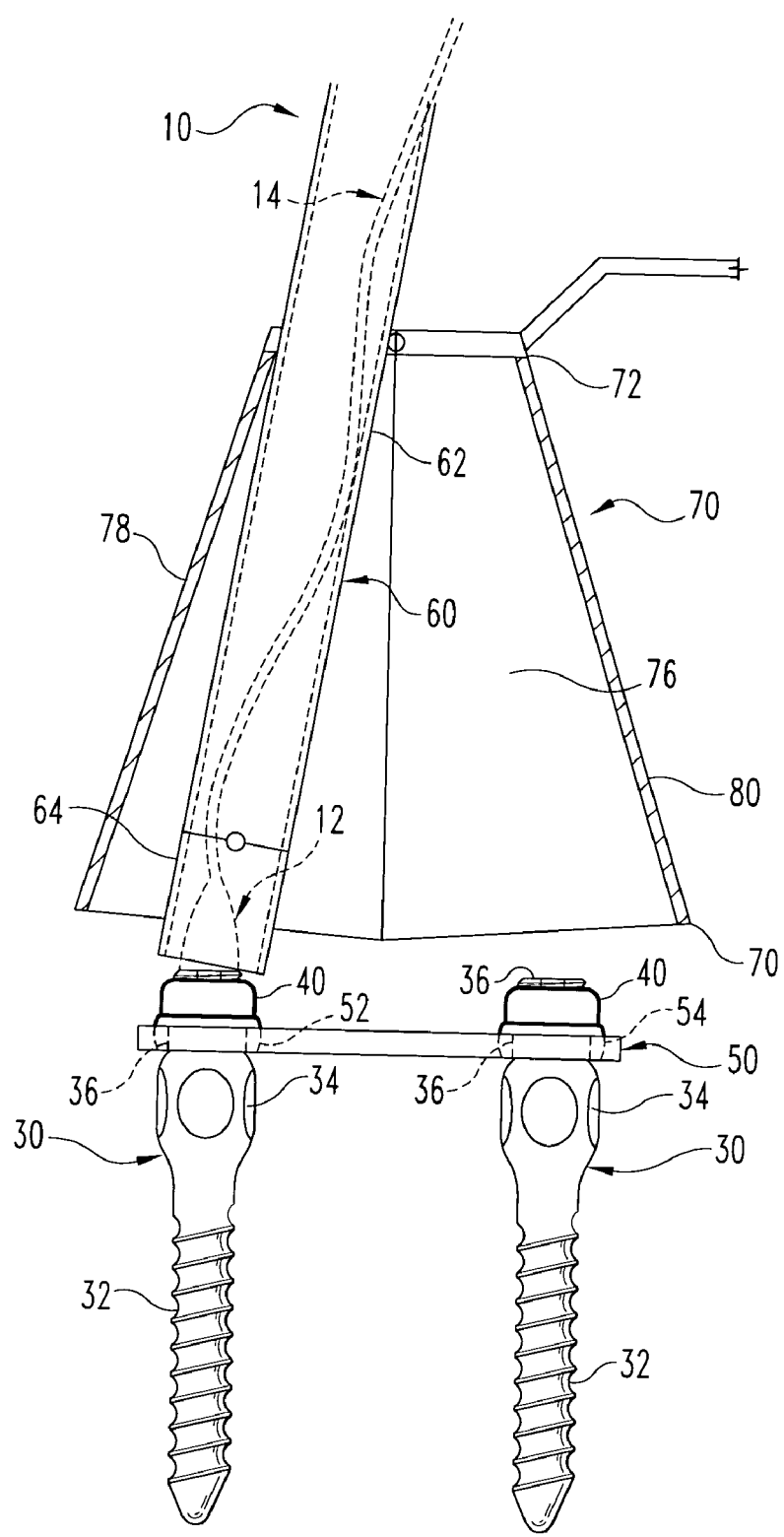
FIG. 7 is an elevation view showing another portion of the technique using the guide member for positioning an implant adjacent the spinal column in a minimally invasive approach.

For embodiments employing a removable guide member 10, a removal instrument 60 can be provided as shown in FIG. 7. After securing implant 50 to anchors 30 with engagement members 40, guide members 10 can be removed with a removal instrument 60. Removal instrument 60 includes a shaft 62 with a passage for receiving guiding portion 14 at least partially therethrough. Removal instrument 60 further includes a distal end portion engageable to connecting portion 12 to apply a removal force thereto, whether it be to unthread connecting portion 12 of guide member 10 from threaded receptacle 38, or to axially withdraw connecting portion 112 of guide member 110 from receptacle 138, or to apply some other removal force as may be required.

It is also contemplated that guiding portion 14 can be tightened to retract or move tissue or other anatomical structures positioned therealong in procedures not employing retractor 70. Tightening of guiding portion 14 to a taut condition can also facilitate movement of the implant therealong toward anchor 30. In still another technique, guiding portions 14 can be coupled to a tensioning device to provide a compression or distraction load to vertebrae 200, 204 prior to securing engagement member 40 thereto. Such loads can be applied to provide compression on implant 206, to correct curvature of the spinal column segment to which implant 50 is to be attached, and/or to increase or decrease the spacing between vertebrae 200, 204.

Figure 8:
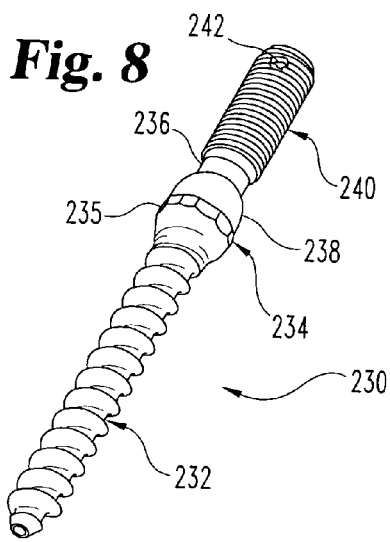
FIG. 8 is a perspective view of another embodiment bone anchor attachable to a guide member.
Figure 9:
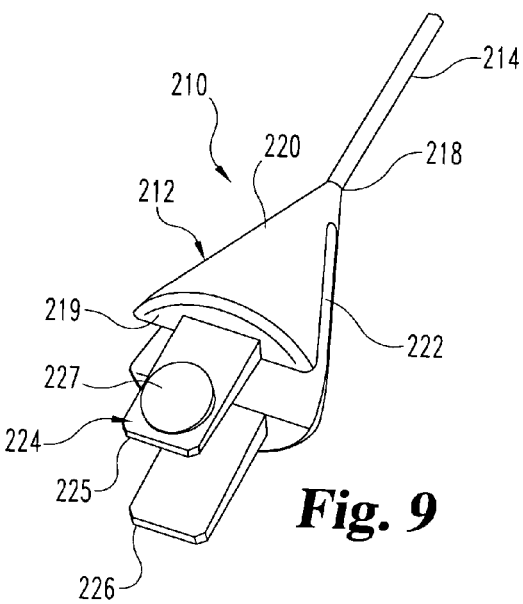
FIG. 9 is a perspective view of a distal portion of another embodiment guide member attachable to the anchor of FIG. 8.
Figure 10:
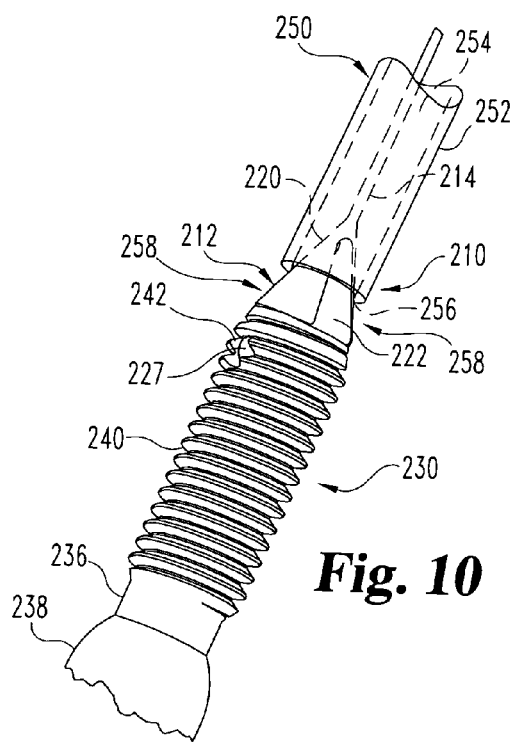
FIG. 10 is a perspective view of the guide member of FIG. 9 attached to the anchor of FIG. 8.

Another embodiment anchor 230 is shown in FIG. 8 that is attachable to a guide member 210, as shown in FIGS. 9 and 10. In the illustrated embodiment, anchor 230 is a bone screw having a distally threaded shaft 232 and an intermediate portion 234. Intermediate portion 234 includes a distal tool engagement portion 235 and a hemi-spherical proximal portion 235 that includes a smooth surface profile. A transition portion 236 extends proximally from proximal portion 235 to a head portion 240.

Head portion 240 extends proximally from proximal portion 235 and includes a proximally opening receptacle for receiving a portion of guide member 210. Head portion 240 further includes an external threaded pattern to facilitate attachment or securement of an implant and/or fastener thereto. An opening 242 extends through the external thread pattern of head portion 240 and is in communication with the proximally opening receptacle. Other embodiments contemplate that opening 242 does not extend through head portion 240, but rather forms a receptacle in the inner wall surface of head portion 240 in communication with the proximally opening receptacle thereof.

Referring to FIG. 9 there is shown a distal portion of guide member 210. Guide member 210 includes a connecting portion 212 and a guiding portion 214. Connecting portion 212 is engageable to a bone anchor, such as bone anchor 230. Guiding portion 214 extends proximally from connecting portion 212 and is adapted to receive an implant to guide the implant therealong to a position adjacent the anchor such as discussed above with respect to guide members 10, 110. Guiding portion 214 can be flexible to facilitate placement of the implant adjacent to the anchor in minimally invasive surgical approaches to the spinal column. Guide member 210 can be attached to anchor 230 prior to insertion of anchor 230 into the patient, or can be attached to the anchor after engagement of the anchor in the patient.

In the illustrated embodiment, connecting portion 212 includes a body 220 that includes a conical shape that tapers proximally from distal end 219 of body 220 to proximal end 218 of body 220. Body 220 can include one or more recesses 222 formed therein to facilitate engagement with a removal or insertion tool and flexing of body 220 for engagement and disengagement with anchor 230. Connector 224 extends distally from body 220. Connector 224 includes a first member 225 and a second member 226 spaced from first member 225. First and second members 225, 226 form plate-like extensions extending distally from distal end 219 of body 220. First member 225 includes an engagement portion 227 extending laterally therefrom. Second member 226 similarly includes an engagement portion (not shown) extending laterally therefrom in a direction opposite engagement portion 227.

Engagement portions 227 are sized for receipt in openings 242 of head portion 240 to secure guide member 210 to anchor 230. First and second members 225, 226 are movable or inwardly deflectable toward one another as connector 224 is inserted into the proximally opening passage of head portion 240 to allow passage of engagement portions therealong. When the engagement portions 227 are aligned with a corresponding opening 242 in head portion 240, first and second members 225, 226 return toward their pre-insertion configuration so that engagement members 227 are received in the corresponding opening 242 of head portion 240 to secure guide member 210 thereto.

Engagement portions 227 can be in the form of cylindrical projections tapered distally so that each includes a distal end of reduced height facilitating insertion into the proximally opening passage of head portion 240. Engagement members 227 can be provided with a proximal end of greater height to engage in openings 242 and resist proximal movement of guide member 210 relative to anchor 230. Distal end 219 can be located relative engagement members 227 so to contact the proximal end surface of head portion 240 when guide member 210 is fully seated on anchor 230. Alternatively, distal end 219 can be located relative engagement members 227 so to be spaced from the proximal end surface of head portion 240 when guide member 210 is fully seated on anchor 230.

In FIG. 10 there is further shown a removal tool 250 to facilitate removal of guide member 210 from anchor 230 after the implant is secured thereto. Removal tool 250 includes a body 252 defining a receptacle or passage 254 to receive connecting portion 212 of guide member 210 therein. Guiding portion 214 can extend into and/or through passage 254 to guide and facilitate placement of a distal end 256 of removal instrument 250 over connecting portion 212.

Distal end 256 is sized to contact body 220 along its tapered outer surface. As removal tool 250 is advanced distally, recess 222 facilitates compression of body 220 by the forces exerted by removal instrument 250. Engagement members 227 are thus moved toward one another, as indicated by arrows 258, for disengagement with openings 242 of head portion 240 of anchor 230. Guide member 210 can then be withdrawn from the surgical site with removal tool 250.

Other embodiments contemplate removal instrument 250 including a distal slot for side loading on guide member 210. Still other embodiments contemplate a removal tool with movable distal end members to apply a removal force to guide member 210. Removal tools can be configured to unthread, compress, expand, cut, or otherwise permit removal of all or a portion of guide member 210 from anchor 230. It is also contemplated that all or a portion of guide member 210 can remain post-operatively attached to anchor 230.

Other embodiments contemplate other mechanisms for engaging the guide members to the anchors. For example, the connecting portion could include a connector with an internal receptacle that fits around all or a portion of the proximal head portion of the anchor for engagement therewith. In another form, the connecting portion is engaged with tissue, bone or other anatomical structures adjacent the bone anchor.

While embodiments of the invention have been illustrated and described in detail in the drawings and foregoing description, the same is to be considered as illustrative and not restrictive in character, it being understood that all changes and modifications that come within the spirit of the invention are desired to be protected.

What is claimed is:

1. A device for guiding an implant to a location adjacent a bone anchor, comprising:
   a guide member including a connecting portion and a guiding portion, said connecting portion including:
      a body extending between a distal end and a proximal end;
      a connector extending distally from said distal end of said body, said connector including resiliently movable engagement portions extending outwardly therefrom in opposite directions from one another for releasably engaging said engagement portions within the bone anchor;
      said guiding portion extends proximally from said proximal end of said body; and
      said body is tapered from said distal end to said proximal end with said distal end sized to transition from the connector to the bone anchor for guiding the implant to the anchor, wherein with said connecting portion adjacent the bone anchor said guiding portion extends proximally from said connecting portion and is adapted to receive the implant, wherein said guiding portion is flexible and positionable between an untaut configuration and a taut configuration as the implant is guided therealong.

2. The device of claim 1, wherein said guiding portion is selected from the group consisting of: a cable, a wire, a tether, a cord, a suture, and a thread.

3. The device of claim 1, wherein said connector includes a pair of extensions extending distally from said body.

4. The device of claim 3, wherein said distal extensions each include a corresponding one of said engagement portions extending therefrom.

5. The device of claim 4, wherein said engagement portions each project laterally from said respective distal extension.

6. The device of claim 4, wherein said distal extensions are deflectable toward one another for insertion into the bone anchor and biased toward a pre-insertion orientation to facilitate said engagement portions engaging the bone anchor and said engagement portions each include a proximal end having a first height projecting from said respective distal extension and said engagement portions taper distally from said proximal end thereof to a distal end thereof having a second height less than said first height.

7. A device for guiding an implant to a location adjacent a bone anchor, comprising:
   a guide member including a connecting portion and a guiding portion, wherein with said connecting portion adjacent the bone anchor said guiding portion extends proximally from said connecting portion and is adapted to receive the implant, said connecting portion including a body comprising a tapered portion to transition between the anchor and said guiding portion, wherein said guiding portion is structured to move between a loose condition for receiving the implant and a taut condition while the implant is guided along said guiding portion to the bone anchor.

8. The device of claim 7, wherein said guiding portion is flexible and movable to any one of a plurality of orientations relative to the anchor as the implant is guided therealong.

9. The device of claim 7, wherein said guiding portion is selected from the group consisting of: a cable, a wire, a tether, a cord, a suture, and a thread.

10. The device of claim 7, wherein said connecting portion includes a connector extending distally from said body adapted to threadingly engage the bone anchor.

11. The device of claim 7, wherein said connecting portion includes a connector extending distally from said body adapted to frictionally engage the bone anchor.

12. The device of claim 7, wherein said connecting portion includes a body and a pair of extensions extending distally from said body, said distal extensions releasably engageable with the bone anchor.

13. The device of claim 12, wherein said distal extensions each include an engagement portion extending therefrom in opposite directions from one another that are engageable with the bone anchor.

14. The device of claim 13, wherein said engagement portions each project laterally from said respective distal extension and said engagement portions each include a proximal end having a first height projecting from said respective distal extension and said engagement portions taper distally from said proximal end thereof to a distal end thereof having a second height less than said first height.

15. The device of claim 13, wherein said distal extensions are deflectable toward one another for insertion into the bone anchor and biased toward a pre-insertion orientation to facilitate said engagement portions engaging the bone anchor.

16. The device of claim 7, wherein said body includes a cylindrical distal portion and said tapered portion extends between said distal portion and said guiding portion.

17. The device of claim 7, wherein said tapered portion extends from a distal end of said body to a proximal end of said body.

18. A device for guiding an implant to a location adjacent a bone anchor, comprising:
   a guide member including a connecting portion and a guiding portion, wherein with said connecting portion adjacent the bone anchor said guiding portion extends proximally from said connecting portion and is adapted to receive the implant, wherein said guiding portion is flexible and movable to any one of a plurality of orientations relative to the anchor as the implant is guided therealong and said connecting portion includes a body and a pair of extensions extending distally from said body, said distal extensions are resiliently movable relative to said body and each includes an engagement portion extending therefrom releasably engageable within the bone anchor, wherein said engagement portions extend outwardly from said distal extensions in opposite directions from one another.

19. The device of claim 18, wherein said guiding portion is selected from the group consisting of: a cable, a wire, a tether, a cord, a suture, and a thread.

20. The device of claim 18, wherein said connecting portion includes a rigid tapered proximal portion forming a continuation of said guiding portion adjacent the bone anchor.

21. The device of claim 18, wherein said engagement portions each project laterally from said respective distal extension and said engagement portions each include a proximal end having a first height projecting from said respective distal extension and said engagement portions taper distally from said proximal end thereof to a distal end thereof having a second height less than said first height.

22. The device of claim 21, wherein said distal extensions are deflectable toward one another for insertion into the bone anchor and biased toward a pre-insertion orientation to facilitate said engagement portions engaging the bone anchor.

23. The device of claim 18, wherein said guiding portion is structured to move between a loose condition and a taut condition.

24. A device for guiding an implant to a location adjacent a bone anchor, comprising:

a guide member including a connecting portion and a guiding portion, wherein with said connecting portion adjacent the bone anchor said guiding portion extends proximally from said connecting portion and is adapted to receive the implant, wherein said connecting portion includes a body comprising a tapered portion forming a substantially uniform transition between the anchor and said guiding portion and said connecting portion includes a body and a pair of extensions extending distally from said body, said distal extensions are resiliently movable relative to said body and each includes an engagement portion extending therefrom releasably engageable within the bone anchor, wherein said engagement portions extend outwardly from said distal extensions in opposite directions from one another.

25. The device of claim 24, wherein said guiding portion is flexible and movable to any one of a plurality of orientations relative to the anchor as the implant is guided therealong.

26. The device of claim 24, wherein said guiding portion is selected from the group consisting of: a cable, a wire, a tether, a cord, a suture, and a thread.

27. The device of claim 24, wherein said engagement portions each project laterally from said respective distal extension and said engagement portions each include a proximal end having a first height projecting from said respective distal extension and said engagement portions taper distally from said proximal end thereof to a distal end thereof having a second height less than said first height.

28. The device of claim 27, wherein said distal extensions are deflectable toward one another for insertion into the bone anchor and biased toward a pre-insertion orientation to facilitate said engagement portions engaging the bone anchor.

29. The device of claim 24, wherein said guiding portion is structured for positioning between an untaut configuration and a taut configuration.

* * * * *